US005192317A

United States Patent [19]
Kalb

[11] Patent Number: 5,192,317
[45] Date of Patent: Mar. 9, 1993

[54] MULTI FOCAL INTRA-OCULAR LENS
[75] Inventor: Irvin M. Kalb, Santa Monica, Calif.
[73] Assignee: Irvin Kalb, Beverly Hills, Calif.
[21] Appl. No.: 866,668
[22] Filed: Apr. 8, 1992

Related U.S. Application Data

[60] Division of Ser. No. 366,638, Jun. 14, 1989, Pat. No. 5,139,519, which is a continuation-in-part of Ser. No. 224,540, Jul. 26, 1988, abandoned.

[51] Int. Cl.$^5$ ............................................. A61F 2/16
[52] U.S. Cl. ........................................ 623/6; 351/161; 351/168
[58] Field of Search .................... 623/6; 351/161, 168, 351/171

[56] References Cited

U.S. PATENT DOCUMENTS

| | | | |
|---|---|---|---|
| 4,556,998 | 12/1985 | Siepser | 623/6 |
| 4,573,998 | 3/1986 | Mazzocco | 623/6 |
| 4,636,211 | 1/1987 | Nielsen et al. | 623/6 |
| 4,637,697 | 1/1987 | Freeman | 351/161 |
| 4,752,123 | 6/1988 | Blaker | 351/161 |
| 4,781,717 | 11/1988 | Grendahl | 623/6 |
| 4,804,361 | 2/1989 | Anis | 623/6 |
| 4,813,955 | 3/1989 | Achatz et al. | 623/6 |
| 4,890,913 | 2/1990 | De Carle | 351/161 |
| 4,898,461 | 2/1990 | Portney | 351/169 |
| 5,089,024 | 2/1992 | Christie et al. | 623/6 |

FOREIGN PATENT DOCUMENTS 3332313 4/1985 Fed. Rep. of Germany .
WO80/03961 7/1986 PCT Int'l Appl. .

OTHER PUBLICATIONS

New Concepts in Circular Posterior Chamber Lenses, Ocular Surgery News, Oct. 1, 1987, Aziz Y. Anis, MD, pp. 16-18.

Primary Examiner—Ronald Frinks
Assistant Examiner—Mary Beth O. Jones
Attorney, Agent, or Firm—Perman & Green

[57] ABSTRACT

The invention comprises an IOL with at least a center zone and two concentrically located ring zones arranged thereabout, the center zone having a distance power correction. The first concentric ring zone has a near power correction and the second concentric zone a distance power correction. In one embodiment the lens body is provided with haptics which act to center the lens body when it is surgically implanted within the posterior lens capsule.

In other embodiments, the lens diameter is increased to mate with the internal dimensions of the posterior lens capsule or is provided with an encircling haptic which bears against the posterior lens capsule.

6 Claims, 2 Drawing Sheets

MULTI FOCAL INTRA-OCULAR LENS

This is a divisional of copending application(s) Ser. No. 07/366,638 filed on Jun. 14, 1989 now U.S. Pat. No. 5,139,519 which was a continuation-in-part of Ser. No. 07/224,540 filed Jul. 26, 1988, abandoned.

FIELD OF THE INVENTION

This invention relates to intra-ocular lenses (IOL) and, more particularly, to an improved multi-focal intra-ocular lens.

BACKGROUND OF THE INVENTION

Over the past several decades, it has become a common place surgical procedure to replace an opacified lens in the human eye with an artificial single power IOL. Such replacements have seen wide success. Until recently, the employment of multi-focal IOL's had not been considered seriously. However, with advances in the state of the art in multi-focal contact lenses, physicians are proceeding with the implantation of multi-focal IOL's.

Some of the more successful contact lenses of the multi-focal type are called "simultaneous image lenses". Those lenses are characterized by an aspheric anterior and/or posterior surface and by a continuously changing power from the para-central area to the mid-periphery. Lenses of this type are described in U.S. Pat. No. 3,031,927 to Wesley; U.S. Pat. No. 3,037,425 to DeCarle and U.s. Pat. No. 4,636,049 to Blaker. The Wesley lens includes a small center zone for near vision surrounded by a concentric distance correction zone. The DeCarle lens includes an opposite construct wherein the distance zone is in the center and is surrounded by the near correction zone. Blaker, describes a lens similar to the Wesley lens, however, he indicates that the near zone center section should be approximately equal to half the pupil area of the eye under average light reading conditions. The latter consideration indicates one of the problems with these lenses—i.e. that they are affected by the pupil size in that the pupil must be large enough to let enough light through the higher add zone of the lens to provide true bifocal action. Lenses of the Wesley/Blaker type are called reverse centrad bifocals.

One significant problem with the reverse centrad bifocals is that during outdoor activities in bright light, or in the presence of a bright illumination at night (e.g. such as driving a car in the presence of oncoming traffic), pupillary constriction reduces the proportion and percentage of rays of light that pass through the distance outer zone thus reducing the quality of distance vision. In fact, if there is sufficient pupillary constriction during the day or as a result of the headlights from oncoming vehicles at night, substantially all distance vision may be lost. This is obviously unacceptable—especially when it is considered that such a loss, when driving a car or as a pedestrian, is life threatening.

Recently, Nielsen at the Center for Eye Surgery in Clearwater, Fla. has implanted bifocal IOL's employing the designs suggested by Wesley and Blaker. Those lenses were implanted in a number of patients and were reported as providing "successful results". (see Ophthalmology Times volume 11, number 9, May 1, 1986, pages 1, 77 and 78).

Nielsen's implanted lenses experience the same defects as the reverse centrad bifocal lenses, i.e. during activities outdoors in bright light or at night when driving a car in oncoming traffic conditions, pupillary constriction reduces the proportion and percentage of rays of light that can be perceived from the distance (outer) zone and thus reduces the quality of distance vision.

German Published Patent Application DE 3332313 A1 (U.S. Pat. No. 4,813,955) describes a multifocal intra-ocular lens wherein the near and far regions of the lens have approximately equal surface proportions and are symmetrically disposed as increasing concentric circles. The patent teaches that the approximate 50/50 ratio of surface areas of near and far correction regions is to be kept constant. This constraint creates problems in low light situations, i.e. at night. As the pupil enlarges, half the light is focused for near vision and half for far vision. This reduces the light utilizable for either far or near vision to one half the available light and significantly reduces the ability to see at night.

If a design is chosen which utilizes a far vision center zone, the lens is restricted to 50% or greater far vision. This design does not offer a combination of dimensions which would allow a more than 50% near vision under preferred reading conditions.

Accordingly it is an object of this invention to provide an improved bifocal IOL which preserves distance vision under all circumstances.

It is a further object of this invention to provide an improved bifocal IOL which preserves distance vision while also enhancing near vision under moderate light conditions.

It is another object of this invention to provide an improved bifocal IOL which is particularly adapted to insertion into the posterior lens capsule.

SUMMARY OF THE INVENTION

The invention comprises an IOL with at least a center zone and two concentrically located ring zones arranged thereabout, the center zone having a distance power correction. The first concentric ring zone has a near power correction and the second concentric zone a distance power correction. In one embodiment the lens body is provided with haptics which act to center the lens body when it is surgically implanted within the posterior lens capsule. In another embodiment, the greater proportion of the lens' correction zones are devoted to distance power corrections.

In a second embodiment, the lens diameter is increased to mate with the internal dimensions of the posterior lens capsule.

DETAILED DESCRIPTION OF THE INVENTION

Figure 1:
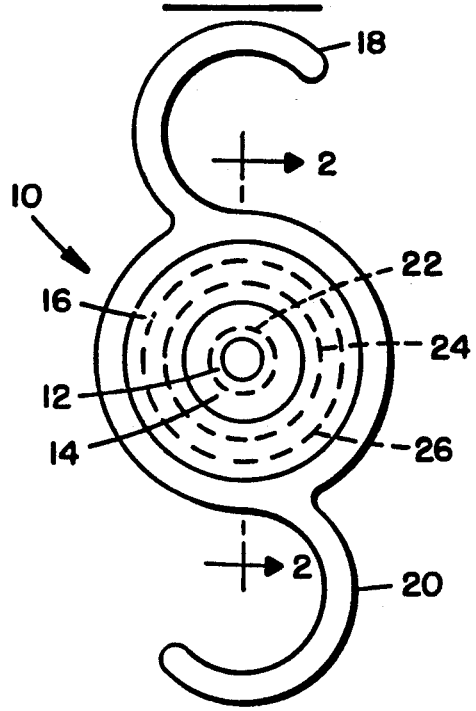
FIG. 1 is a plan view of an IOL embodying the invention.

Referring now to FIG. 1, there is shown a plan view of a bifocal IOL particularly adapted to implantation in the posterior lens capsule. Lens body 10 is formed of a single piece of plastic material, such as silicone, PMMA, other acrylates, polycarbonates, hydrogels or similar optically suitable materials. The lens is comprised of three correction zones, a circular zone 12 having a distance power correction; a concentrically arranged near power correction zone 14 and a second concentrically arranged distance power correction zone 16. A pair of haptics 18 and 20 are integrally formed with lens 10 and provide the centering facility for the lens when it is implanted in the posterior lens capsule. In the conventional manner, haptics 18 and 20 are flexible and bear against the inner surfaces of the lens capsule to center lens 10 subsequent to its implantation.

Dotted circles 22, 24 and 26 are representations of average pupillary openings under expected bright light conditions, average light conditions and low light conditions respectively. Pupillary openings 22, 24 and 26 are approximately 2 mm, 4 mm, and 6 mm in diameter. The 2 mm dimension is the smallest pupillary opening achieved under extreme bright light conditions or with the use of drugs to restrict the pupil, i.e., Miacol Pilocarpine. Under moderate light conditions the pupil ranges from 2.7 to 4.0 mm. The 4 mm dimension approximates the largest pupil opening involved for near vision. In dark conditions, the pupil expands beyond 4 mm. The 6 mm dimension approximates an average pupil in low light conditions. The preferred dimensions of the correction zones of IOL 10 are indicated in the side view of lens 10 in FIG. 2. Center zone 12 is approximately 1.0 mm in diameter; first concentric near zone 14 has a preferred radial width in the range of 1.15 mm to 2.12 mm and the outer diameter of lens 10 has a preferred overall range of from 5 mm to 9 mm.

With the above noted zone dimensions, it can be seen that under expected bright light conditions, the diameter of zone 12 is less than the expected minimum pupillary diameter 22 and assures continual distance vision. Under low light (dark) conditions, the width of concentric zone 16 is such as to enable substantial amounts of distance light to enter pupillary opening 26. It can further be seen that if the pupil expands further than is shown by dotted line 26, that distance corrected light entering the pupillary opening increases as the square of the radius thus enabling improved distance vision even under low light conditions.

Figure 3:
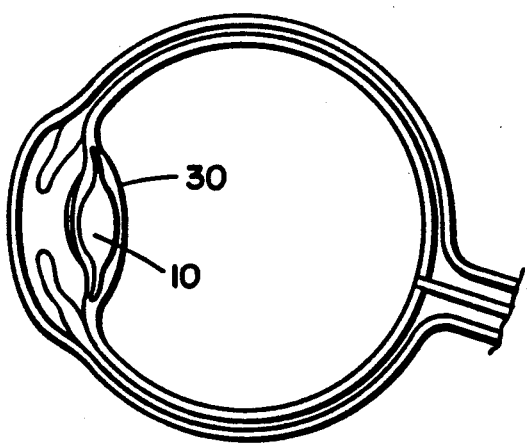
FIG. 3 is a section view of an eye with the lens of this invention implanted in the posterior lens capsule.
Figure 2:
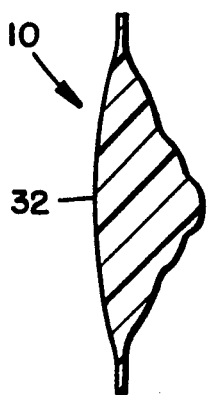
FIG. 2 is a sectional view of the invention taken along line 2—2.

Referring now to FIG. 3, lens 10 is shown implanted in the posterior lens capsule 30. The focal planes for all of the segments of IOL 10 fall on the macular portion of the retina and provide simultaneous images. As shown in FIG. 2, posterior surface 32 of lens 10 has a convex form which conforms to the posterior portion of lens capsule 30 to thereby avoid protein build up between the posterior portion of the lens and the capsule. The posterior surface may also be configured as a plane or meniscus.

Figure 4:
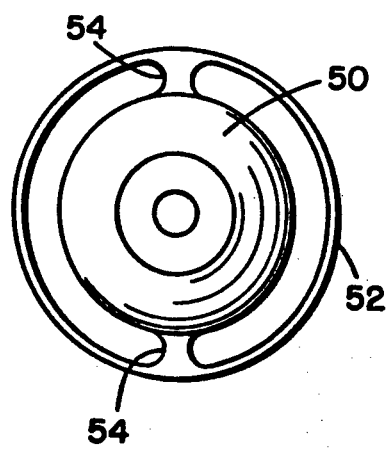
FIG. 4 is a plan view of an IOL embodying the invention with a circular haptic.

Another IOL lens configuration made in accordance with this invention is shown in FIG. 4 and includes a central optic 50, a haptic 52 which fully encircles the optic and one or, more struts 54 which attach the haptic to optic 50. Optic 50 is further provided with identical correction ring zones to the IOL shown in FIG. 1.

Figure 5:
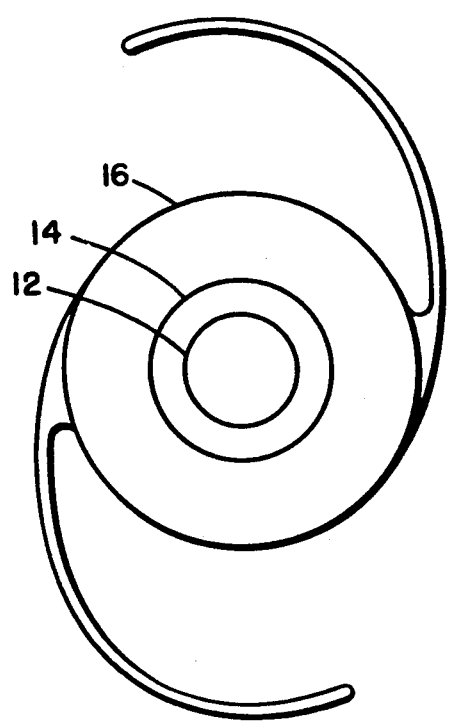
FIG. 5 is a plan view of an IOL embodying the invention with enhanced bright and low light distance power corrections.
Figure 6:
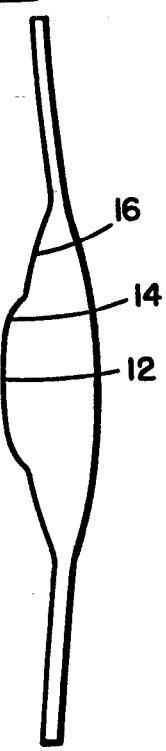
FIG. 6 is a side view of the lens of FIG. 5 and shows representative dimensions for the lens' correction zones.

Referring now to FIGS. 5 and 6, an IOL is shown wherein the diameter of central distance correction zone 12 is increased to approximately 2.1 mm. This enables the maximum amount of distance corrected light to enter the eye under extreme bright light conditions and preserves the best available distance vision under the circumstances. It can be appreciated that the diameter of the distance correction zone 12 still has a diameter less than the average pupil diameter (3.0 mm) under moderate light conditions and provides true bifocal action.

Figure 7:
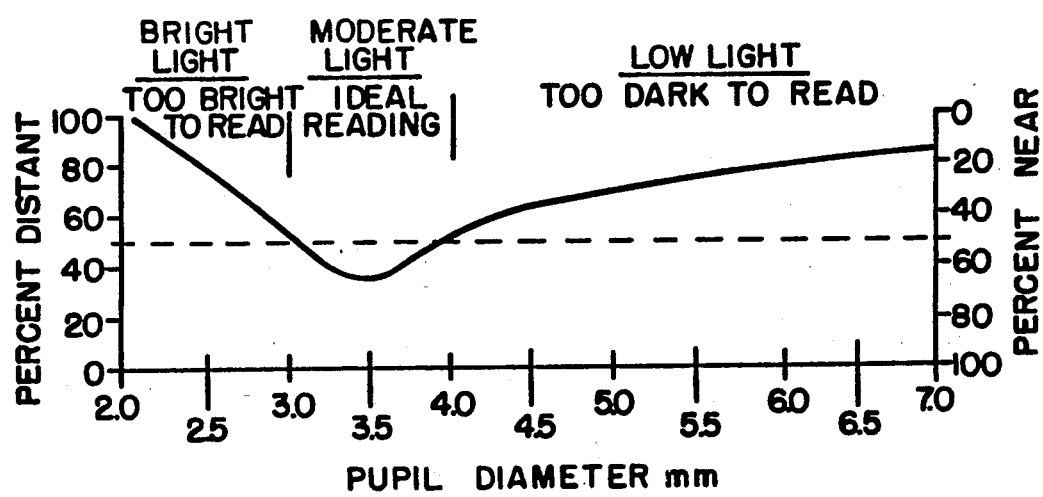
FIG. 7 is a plot which shows the dominant affect of the distance correction zones of a lens incorporating the invention.

From an examination of the IOL's shown in FIGS. 1 and 2 and FIGS. 5 and 6, it can be seen that in each, a greater percentage of lens area is devoted to distance vision than near vision. This is especially important in low light (dark) conditions, where it is desired to maximize the light gathering distance correction surface area. A plot is shown in FIG. 7, of the percentage of area available for distance and near correction under various pupil diameters for a lens incorporating the invention, e.g., such as the lens of FIGS. 5 and 6. Under most conditions, except for moderate light conditions which are optimal for reading (pupil diameters 3.0–4.0 mm), more than 50% of the IOL's light gathering surface area exposed by the pupil is devoted to distance correction. This assures maximum user safety while providing good light gathering capabilities for reading.

It should be understood that the foregoing description is only illustrative of the invention. Various alternatives and modifications can be devised by those skilled in the art without departing from the invention. For instance, while the IOL of this invention has been shown implanted in the posterior lens capsule, it may also be implanted in the anterior chamber or in the iris plane. Furthermore, while only two haptics are shown, more may be employed (e.g. three or four) or the lens can be made as a disk which is either flexible, rigid or a combination thereof. In such latter construct, the diameter of the disk is adjusted to mate with the internal dimensions of the posterior lens capsule.

While the ring correction zones have been shown as arranged on the anterior surface of the optic, it is also contemplated that the ring zones may be on the posterior surface of the optic or there could be a combination of rings on the posterior and anterior surfaces which, in combination, provide the desired corrections. If all or some of the ring zones are resident on the posterior surface of the optic, the anterior surface may be concave, plane or convex.

Further, the lens may be constructed of multiple pieces with the haptic constructed from material the same as the optic (e.g., PMMA) or a different material (e.g., polypropylene). These materials are permanently attached to the optic using suitable attachment means.

Accordingly, the present invention is intended to embrace all such alternatives, modifications and variances which fall within the scope of the appended claims.

I claim:

1. An intra-ocular lens for eye implantation comprising:
    a lens body having optical portions comprised of a unitary material and additionally comprising at least a center zone and inner and outer concentrically located ring correction zones, said center zone having a distance power correction, said inner ring correction zone having a near power correction and said outer ring correction zone having a distance power correction, said center and outer ring correction zones sized to assure that only under a bright light and lower light conditions does more than 50% of light focused on the eye's retina pass through distance power correction zones, said center zone having a diameter which assures, at a pupil diameter of 2.0 millimeters, that more than 75% of light focused on said retina passes through said center zone, thereby assuming continuance of distance vision under bright light conditions.

2. The invention as defined in claim 1 wherein the outer diameter of the outer concentrically located ring correction zones exceeds the average pupil diameter under expected low light conditions.

3. The intra-ocular lens as defined in claim 2 wherein said lens body is provided with haptics for centering said lens body when it is surgically implanted in the eye.

4. An intra-ocular lens for eye implantation comprising:
a lens body having optical portions comprised of a unitary material and additionally comprising at least a center zone and inner and outer concentrically located ring correction zones, said center zone having a distance power correction, said inner ring correction zone having a near power correction and said outer ring correction zone having a distance power correction, said center and outer ring correction zones sized to assure that under bright light and low light conditions, more than 75% of light focused on the eye's retina passes through distance power correction zones, and under moderate light conditions wherein reading is accomplished, more than 50% of light focused on the eye's retina passes through said inner ring correction zone.

5. The invention as defined in claim 1 wherein the outer diameter of the outer concentrically located ring correction zones exceeds the average pupil diameter under expected low light conditions.

6. The intra-ocular lens as defined in claim 2 wherein said lens body is provided with haptics for centering said lens body when it is surgically implanted in the eye.

* * * * *

UNITED STATES PATENT AND TRADEMARK OFFICE
CERTIFICATE OF CORRECTION

PATENT NO. : 5,192,317
DATED : March 9, 1993
INVENTOR(S) : Irvin M. Kalb

It is certified that error appears in the above-identified patent and that said Letters Patent is hereby corrected as shown below:

IN THE CLAIMS

In Claim 1, col. 5, line 3 delete "lower" and insert --low--.

In Claim 5, col. 6, line 14 delete "1" and insert --4--.

In Claim 6, col. 6, line 18 delete "2" and insert --5--.

Signed and Sealed this

Seventh Day of December, 1993

Attest:

BRUCE LEHMAN

Attesting Officer

Commissioner of Patents and Trademarks